United States Patent [19]
Kersten

[11] 4,262,671
[45] Apr. 21, 1981

[54] AIRWAY CONNECTOR

[75] Inventor: Jean Kersten, Villers St. Amand, Belgium

[73] Assignee: Baxter Travenol Laboratories, Inc., Deerfield, Ill.

[21] Appl. No.: 89,806

[22] Filed: Oct. 31, 1979

[51] Int. Cl.³ .............................................. A61J 1/08
[52] U.S. Cl. ................................................ 128/272.3
[58] Field of Search ............ 128/272.3, 272, 218 NV, 128/221, 247; 141/19–28, 329, 330

[56] References Cited

U.S. PATENT DOCUMENTS

| | | | |
|---|---|---|---|
| 3,938,520 | 2/1976 | Scislowicz et al. | 128/272.3 |
| 4,133,314 | 1/1979 | Bloom et al. | 128/272.3 |

FOREIGN PATENT DOCUMENTS 1096431  6/1955  France ................................. 128/272.3

Primary Examiner—John D. Yasko
Attorney, Agent, or Firm—Paul C. Flattery; John P. Kirby, Jr.; George H. Gerstman

[57] ABSTRACT

An airway connector is provided for withdrawing solutions from bottles and comprises a spike having a solution flow passage and an air inlet passage, with both passages opening at the tip of the spike. The spike carries a body member having a filter chamber extending radially outwardly from the spike and being positioned eccentrically with respect to the axis of the spike. The body member defines a portion of the air inlet passage with the air inlet passage portion extending angularly through the body member to communicate with the filter chamber. A hydrophobic filter is located in the filter chamber with the filter having a smaller volume than the volume of the filter chamber to provide an air space communicating with the air inlet passage.

15 Claims, 5 Drawing Figures

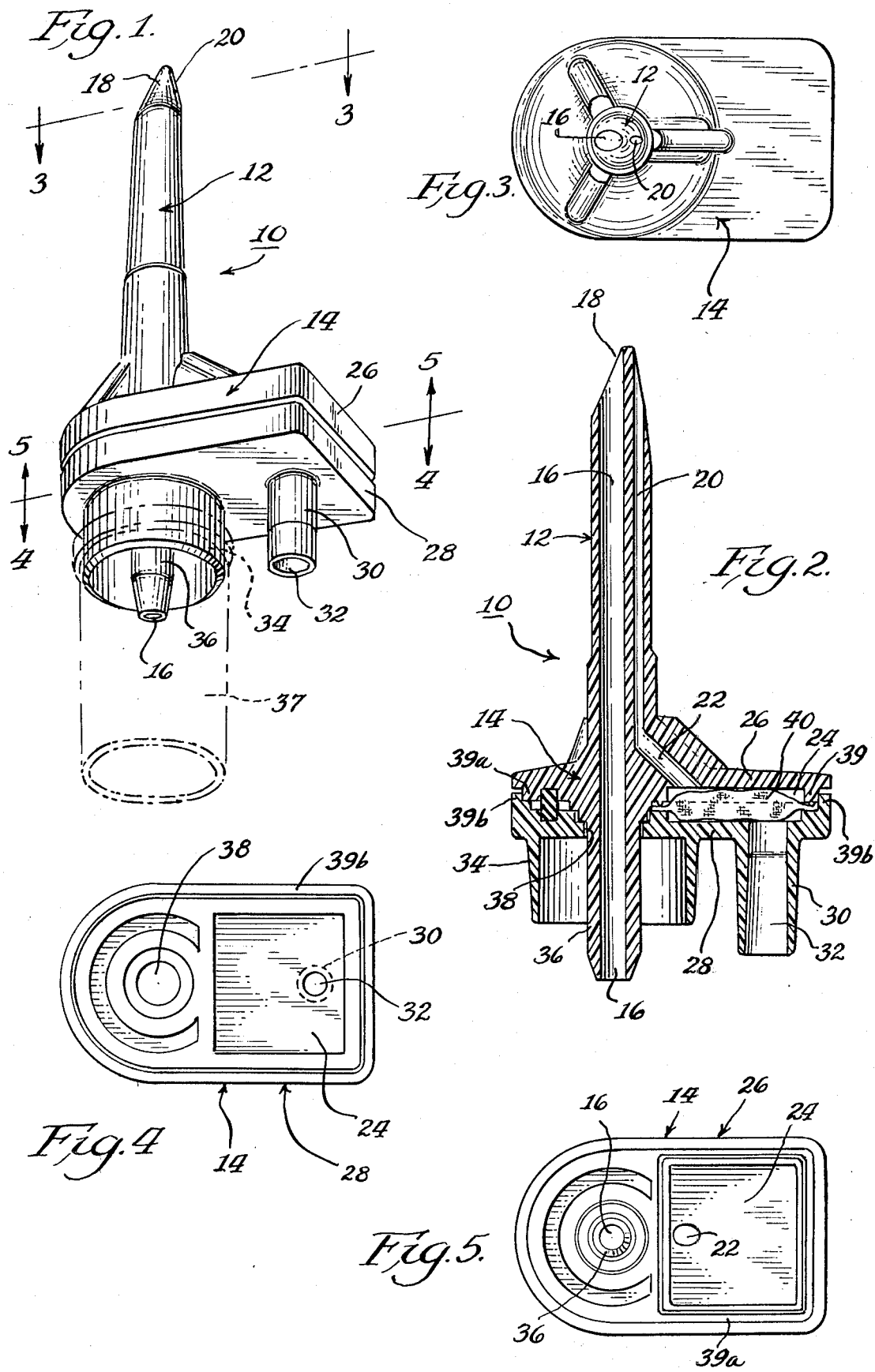

4,262,671

AIRWAY CONNECTOR

BACKGROUND OF THE INVENTION

The present invention concerns a novel airway connector, and, more particularly, an airway connector that may be inserted through a bottle closure to withdraw fluid from the bottle and at the same time permit filtered air to enter the bottle.

Airway connectors are known in which a spike having a solution flow passage and an air inlet passage is inserted into a bottle closure to enable simultaneous entry of air into the bottle and withdrawal of fluid from the bottle. Typically, the air inlet passage contains a filter and such airway connectors are often used in the dispensing of medical solutions. An example of a prior art airway connector is disclosed in Burke U.S. Pat. No. 3,359,977 and another airway connector is illustrated in U.S. Pat. No. DES 229,518.

Often, an airway connector is utilized for insertion into a bottle closure which closure includes an injection site. It is advantageous for the operator to be able to have easy access to the injection site while the airway connector remains inserted in the bottle closure. Therefore, it is an object of the present invention to provide an airway connector that is suitably constructed to enable easy access to an injection site carried by a bottle closure when the airway connector is inserted through the bottle closure.

Another object of the present invention is to provide an airway connector that permits simple plugging of the air inlet passage so that the airway connector may be used as a regular spike without requiring entry of air into the container. In this manner, an airway connector may be used as a spike for a collapsible plastic solution container which does not require the entry of air when the solution is being removed therefrom.

Another object of the present invention is to provide an airway connector that is simple in construction and is easy to manufacture.

A further object of the present invention is to provide an airway connector that is readily adaptible for carrying a drip chamber.

A further object of the present invention is to provide an airway connector which has a hydrophobic filtered air inlet passage with means for avoiding filter blockage.

Other objects and advantages of the present invention will become apparent as the description proceeds.

SUMMARY OF THE INVENTION

In accordance with the present invention, an airway connector is provided for use in withdrawing solutions from bottles. The airway connector comprises a spike defining a solution flow passage and also defining an air inlet passage. The improvement comprises the spike being formed as an integral member, with the solution flow passage and the air inlet passage opening at a tip which is adapted for inserting into a bottle closure.

A body member is carried by the spike, with the body member including a filter chamber extending radially outwardly from the spike. The filter chamber is eccentric to the axis of the spike. The body member defines a portion of the air inlet passage, with the air inlet passage portion extending angularly to communicate with the filter chamber.

In the illustrative embodiment, the solution flow passage extends parallel to the axis of the spike throughout its length and the inlet passage extends parallel to the solution flow passage through the spike and then angularly through the body member to communicate with the filter chamber. A hydrophobic filter is located in the filter chamber, with the filter having a smaller volume than the volume of the filter chamber to provide an air space communicating with the air inlet passage. By utilizing this air space in communication with an air inlet passage that has a 1 mm. diameter, filter blockage is avoided because the air inlet bore generates sufficient superficial forces to avoid liquid flowing into the filter chamber.

A more detailed explanation of the invention is provided in the following description and claims, and is illustrated in the accompanying drawings.

BRIEF DESCRIPTION OF THE DRAWINGS

FIG. 1 is a perspective view of an airway connector constructed in accordance with the principles of the present invention;

FIG. 2 is a cross-sectional elevation thereof;

FIG. 3 is a top view thereof, taken along the plane of the line 3—3 of FIG. 1;

FIG. 4 is a view thereof, taken along the plane of the line 4—4 of FIG. 1; and

FIG. 5 is a view thereof, taken along the plane of the line 5—5 of FIG. 1.

DETAILED DESCRIPTION OF THE ILLUSTRATIVE EMBODIMENT

Referring to the drawings, airway connector 10 is molded of plastic such as a polyester, in a two-piece construction. The airway connector includes a spike 12 and a body portion 14 carried by spike 12.

Spike 12 defines a solution flow passage 16 which opens at tip 18 and also an air inlet passage 20 which opens at tip 18. Solution flow passage 16 extends through the spike to form a bore that is parallel to the axis of the spike. Air inlet passage 20 extends parallel to solution flow passage 16 along the front of the spike, but at the body portion 14 angles to form air inlet passage portion 22 communicating with a filter chamber 24. Filter chamber 24 extends radially outwardly from spike 12 and, as can be readily seen from the drawings, the filter chamber is eccentric to the axis of the spike 12.

By placing the filter chamber in the off-center position as illustrated, the airway connector may be inserted into a bottle stopper that carries an injection site, without blocking the injection site. Thus, the filter chamber portion will extend to one side of the bottle stopper while the operator may have easy access to the injection site carried by the bottle stopper.

Filter chamber 24 is defined between the top portion 26 of body member 14 and the bottom portion 28 of body member 14. Bottom portion 28 also carries a luer connector 30 having a bore 32 that communicates with filter chamber 24, and a drip chamber sleeve 34 which is adapted to surround rear extension 36 of sleeve 12. A drip chamber 37 (FIG. 1) may be fastened to drip chamber sleeve 34 as illustrated.

To provide simplicity and ease in manufacturing, the airway connector is formed from only two unitary sections. These sections are fastened together by means of ultrasonic welding in the illustrative embodiment. The first of the two sections comprises spike 12 and top portion 26 of body member 14, while the second of the two sections comprises bottom portion 28 of body member 14 which bottom portion carries luer connector 30 and drip chamber sleeve 34. By referring to FIG. 2 it can be seen that bottom portion 28 defines an opening 38 which receives the rear extension 36 of spike 12. Top portion 26 carries a downwardly extending tongue 39a which fits snugly within upwardly extending peripheral wall 39b of bottom portion 28.

A hydrophobic filter 40 is located within filter chamber 24 and it can be seen that filter 40 lies directly within the air inlet path consisting of luer bore 32, filter chamber 24, passage 22 and passage 20. Filter 40 has a smaller volume than the volume of filter chamber 20 thereby providing an air space above the filter communicating with passage 22. In the illustrative embodiment, air inlet passage 20 has a diameter of 1 mm., and the cooperation of passage 20 and the air space in chamber 24 operate to avoid filter blockage by fluid collection above the filter. In normal applications, the 1 mm. bore opening for the air inlet will generate sufficient superficial force to avoid inflow of liquid.

It can be seen that body member 14 forms a housing that lies generally perpendicular to the axis of spike 12. The construction illustrted with the perpendicular housing and offset filter chamber enables the provision of an angular passage 22 which permits easier molding because there is less chance of the molding pin breaking or of misalignment.

Luer connector 30 has been found useful to permit a bulb to be attached to luer connector 30, with the bulb being squeezed to increase the pressure and permit faster outflow of the fluid within the bottle. Bore 32 may be easily plugged so that connector 10 may be used as a regular spike very easily and not be used as an airway connector.

In the illustrative embodiment, drip chamber 37 is pressure fitted to sleeve 34 and is also solvent sealed. Although ultrasonic welding of the two sections forming the airway connector is preferred, other fastening techniques may be used if desired.

It is seen that an airway connector has been provided that is simple in construction and is easy to manufacture. Further, the airway connector of the present invention is constructed so that when inserted into the bottle, a bottle closure carrying an injection site will not be blocked. Although an illustrative embodiment of the invention has been shown and described, it is to be understood that various modifications and substitutions may be made by those skilled in the art without departing from the novel spirit and scope of the present invention.

What is claimed is:

1. An airway connector for use in withdrawing solutions from bottles and comprising a spike defining a solution flow passage and also defining an air inlet passage, the improvement comprising:

said spike being formed as an integral member with said solution flow passage and said air inlet passage opening at a tip which is adapted for inserting through a bottle closure;

a body member carried by said spike, said body member including a filter chamber extending radially outwardly from said spike, said filter chamber being eccentric to the axis of said spike;

said body member carrying a drip chamber sleeve which surrounds the rear end of said spike, a drip chamber connected to said sleeve;

said body member defining a portion of said air inlet passage with said air inlet passage portion extending angularly in a direction that is opposite from said tip to communicate with said filter chamber; and a filter located within said filter chamber, said filter having a surface area that is substantially greater than the cross-sectional area of the air inlet passage, with the major surface area of said filter lying in a plane that is generally perpendicular to the axis of said spike.

2. An airway connector described in claim 1; said spike having a tubular extension rearward of said body member.

3. An airway connector described in claim 1, said solution flow passage and said air inlet passage extending parallel to the axis of the spike.

4. An airway connector as described in claim 1, said airway connector being formed from only two unitary sections fastened together, one of said two sections comprising said spike and a top portion of said body member and the other of said two sections comprising a bottom portion of said body member.

5. An airway connector as described in claim 4, wherein said two unitary sections are sonically welded together.

6. An airway connector as described in claim 1, said solution flow passage extending parallel to the axis of said spike throughout its length, said inlet passage extending parallel to said solution flow passage along said spike and then extending through said body member angularly to communicate with said filter chamber.

7. An airway connector as described in claim 1, including a hydrophobic filter located in said filter chamber with said filter having a smaller volume than the volume of said filter chamber to provide an air space communicating with said air inlet passage, said air inlet passage having a diameter of about 1 mm.

8. An airway connector as described in claim 1, said body member forming a housing that lies generally perpendicular to the axis of the spike.

9. An airway connector for use in withdrawing solutions from bottles and comprising a spike defining a solution flow passage and also defining an air inlet passage, the improvement comprising:

said spike being formed as an integral member with said solution flow passage and said air inlet passage opening at a tip which is adapted for inserting through a bottle closure;

a body member carried by said spike, said body member including a filter chamber extending radially outwardly from said spike, said filter chamber being eccentric to the axis of said spike;

said spike having a tubular extension rearward of said body member;

said solution flow passage extending parallel to the axis of said spike throughout its length, said inlet passage extending parallel to said solution flow passage through said spike and then extending angularly in a direction that is opposite from said tip and through said body member to communicate with said filter chamber;

said body member carrying a luer connector extending rearwardly from said filter chamber and in communication therewith;

said body member carrying a drip chamber sleeve which surrounds the rear end of said spike, a drip chamber connected to said sleeve; and a hydrophobic filter located in said filter chamber with said filter having a smaller volume than the volume of said filter chamber to provide an air space communicating with said air inlet passage;

said filter having a surface area that is substantially greater than the cross-sectional area of the air inlet passage, with the major surface area of the filter lying in a plane that is generally perpendicular to the axis of said spike.

10. An airway connector as described in claim 9, said airway connector being formed from only two unitary sections fastened together, one of said two sections comprising said spike and a top portion of said body member and the other of said two sections comprising a bottom portion of said body member.

11. An airway connector for use in withdrawing solutions from bottles and comprising a spike defining a solution flow passage and also defining an air inlet passage, the improvement comprising;

said spike being formed as an integral member with said solution flow passage and said air inlet passage opening at a tip which is adapted for inserting through a bottle closure;

a body member carried by said spike, said body member including a filter chamber extending radially outwardly from said spike;

said spike having a tubular extension rearward of said body member;

said airway connector being formed from only two unitary sections fastened together, one of said two sections comprising said spike and the top portion of said body member and the other of said two sections comprising a bottom portion of said body member;

said body member carrying a drip chamber sleeve which surrounds the rear end of said spike;

a drip chamber connected to said sleeve; and a hydrophobic filter located in said filter chamber with said filter having a smaller volume than the volume of said filter chamber to provide an air space communicating with said air inlet passage;

said filter having a surface area that is substantially greater than the cross-sectional area of the air inlet passage, with the major surface area of the filter lying in a plane that is generally perpendicular to the axis of said spike.

12. An airway connector as described in claim 11, wherein said body member forms a housing that lies generally perpendicular to the axis of the spike and said filter chamber is positioned eccentric to the axis of said spike.

13. An airway connector for use in withdrawing solutions from bottles and comprising a spike defining a solution flow passage and also defining an air inlet passage, the improvement comprising:

said spike being formed as an integral member with said solution flow passage and said air inlet passage opening at a tip which is adapted for inserting through a bottle closure;

a body member carried by said spike, said body member including a filter chamber extending radially outwardly from said spike, said filter chamber being eccentric to the axis of said spike;

said body member carrying a luer connector extending rearwardly from said filter chamber and in communication therewith;

said body member defining a portion of said air inlet passage with said air inlet passage portion extending angularly in a direction that is opposite from said tip to communicate with said filter chamber; and a filter located within said filter chamber, said filter having a surface area that is substantially greater than the cross-sectional area of the air inlet passage, with the major surface area of said filter lying in a plane that is generally perpendicular to the axis of said spike.

14. An airway connector for use in withdrawing solutions from bottles and comprising a spike defining a solution flow passage and also defining an air inlet passage, the improvement comprising:

said spike being formed as an integral member with said solution flow passage and said air inlet passage opening at a tip which is adapted for inserting through a bottle closure;

a body member carried by said spike, said body member including a filter chamber extending radially outwardly from said spike, said filter chamber being eccentric to the axis of said spike;

said body member carrying a drip chamber sleeve which surrounds the rear end of said spike, a drip chamber connected to said sleeve;

said body member defining a portion of said air inlet passage with said air inlet passage portion extending angularly in a direction that is opposite from said tip to communicate with said filter chamber; and a filter located within said filter chamber, said filter having a surface area that is substantially greater than the cross-sectional area of the air inlet passage.

15. An airway connector for use in withdrawing solutions from bottles and comprising a spike defining a solution flow passage and also defining an air inlet passage, the improvement comprising:

said spike being formed as an integral member with said solution flow passage and said air inlet passage opening at a tip which is adapted for inserting through a bottle closure;

a body member carried by said spike, said body member including a filter chamber extending radially outwardly from said spike, said filter chamber being eccentric to the axis of said spike;

said body member carrying a luer connector extending rearwardly from said filter chamber and in communication therewith;

said body member defining a portion of said air inlet passage with said air inlet passage portion extending angularly in a direction that is opposite from said tip to communicate with said filter chamber; and a filter located within said filter chamber, said filter having a surface area that is substantially greater than the cross-sectional area of the air inlet passage.

* * * * *